United States Patent
Dubey et al.

(10) Patent No.: US 6,387,678 B1
(45) Date of Patent: May 14, 2002

(54) STABLE ESTERASE OBTAINED FROM PALMAROSA

(75) Inventors: Vinod Shanker Dubey; Rajesh Luthra; Ali Arif Naqvi; Sushil Kumar, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/535,516

(22) Filed: Mar. 24, 2000

(51) Int. Cl.[7] .................................................. C12N 9/16
(52) U.S. Cl. ........................................................ 435/196
(58) Field of Search .......................................... 435/196

(56) References Cited

PUBLICATIONS

Lim et al., "Isolation and Characterization of Pectin methy-lesterase from Papaya", Arch. Biochem. Biophys. 307 (1) : 15–20 (1993).*

Zhang et al., Iosenzymes of Esterase of Lemongras (Cymbopogon), Zhongcaoyao 24 (10) : 524–526 (1993).*

Antibody Techniques, ed. Malik et al., Academic Press, p. 71 and table of contents (1994).*

* cited by examiner

Primary Examiner—Sandra E. Saucier
(74) Attorney, Agent, or Firm—Darby & Darby

(57) ABSTRACT

A novel esterase, cleaving acyclic monoterpenyl esters into their monoterpenols, has been detected in the crude enzymic preparation of palmarosa (*Cymbopogon martinii*) inflorescence. The extraction and assay condition for the enzyme has been standardized. The esterase enzyme has shown maximum activity in the alkaline pH range, with optimum temperature at 30° C. using geranyl acetate (acyclic monoterpenyl acetate) as substrate. Time course hydrolysis of geranyl acetate using crude enzymic preparation revealed that after 24 hours of incubation approximately 75% geranyl acetate was hydrolyzed. The crude esterase enzyme, when stored at 4° C., was quite stable for one week with 40% loss of activity. The enzyme also has the capability to hydrolyze other acyclic monoterpenyl esters such as geranyl formate and citronellyl acetate, which are normally present in several aromatic plant species.

7 Claims, 3 Drawing Sheets

STABLE ESTERASE OBTAINED FROM PALMAROSA

FIELD OF THE INVENTION

The present invention relates to a stable esterase enzyme and to a process for the extraction thereof from a natural source, and to the use thereof for the cleaving of acyclic monoterpenyl esters into their monoterpenols. More particularly, the present invention relates to a process for the extraction of a novel and stable esterase from the inflorescence of palmarosa (*Cymbopogon martinii*), which can be used to cleave acyclic monoterpenyl esters into their monoterpenols.

BACKGROUND OF THE INVENTION

Monoterpenyl esters are particularly widespread as the major oil components of several plant species and as minor components in many essential oils. Further more these influence the quality of essential oil distilled from such plants. As most of the aromatic plants are known by its high monoterpenyl alcohol contents in their oils, the presence of monoterpenyl esters in some aromatic plants alter the flavour characteristics of these oils, and thereby reducing their price value in the international market.

In conventional industrial processes, the monoterpenyl esters are hydrolyzed chemically by treatment with alkali (e.g. 10% alcoholic KOH) to produce the monoterpenols. The monoterpenols produced by such methods are not preferred by the perfumery industry, because alkali treatment alters their flavour characteristic. There is only one report in Mentha species, which describes the conversion of cyclic monoterpenyl acetates into their monoterpenols through cell suspension cultures [Werrmann and Knorr, *J. Agric. Food Chem.* 41: 517–520 (1993)], Bioconversion methods through plant/microbial enzymes have been frequently used for the production of the various secondary metabolites including essential oil constituents. Freely suspended and immobilized plant cells or enzymic preparations can be used for such bioconversion purposes. The employment of isolated plant enzymes was found to be the most promising because it produces a single compound through bioconversion. In addition, the precursors that cannot enter into living cells can be successfully converted using isolated enzymes. Plant enzymes are generally able to catalyze the reactions stereospecifically resulting in chirally pure products, and they can also perform regiospecific modifications that are not easily carried out by chemical synthesis or by microorganisms [Pras et al., *Plant Cell, Tissue and Organ Culture* 43: 117–121 (1995)]However, there are no such reports on the bioconversion of acyclic monoterpenyl esters into their monoterpenols.

OBJECTS OF THE INVENTION

Accordingly, the main object of the present invention is to provide a novel and stable esterase enzyme that hydrolyses monoterpenyl esters to yield acyclic monoterpenols.

It is another object of the invention to provide a process for the extraction of such novel and stable esterase enzyme from a natural plant source such as palmarosa inflorescence.

It is a further object of the invention to provide a stable esterase enzyme that is capable of cleaving monoterpenyl esters into their respective acyclic monoterpenols.

The novel esterase enzyme mentioned in this invention yields acyclic monoterpenols through hydrolysis of its corresponding monoterpenyl esters. The enzyme can also be useful to hydrolyze the oils containing mixture of acyclic monoterpenyl esters (such as citronella oil) into their monoterpenyl alcohols. The non-specific nature of this novel esterase can be exploited to convert acyclic monoterpenol esters into their corresponding monoterpenols commercially through immobilizing the enzyme.

It is another object of the present invention to develop a process for the extraction of a novel and stable esterase enzyme from a natural source, which is useful for cleaving acyclic monoterpenyl esters into their corresponding monoterpenyl alcohols.

It is a further object of the invention to provide a novel stable esterase that shows a linear increase in activity along with protein concentration.

It is yet another object of the invention to provide a site specific monoterpenyl ester hydrolase capable of removing the terminal ester group of acyclic monoterpenyl esters thereby producing monoterpenyl alcohols.

It is another object of the invention to provide a stable esterase derived from a natural source that is useful for the hydrolysis of acyclic monoterpenyl esters thereby recovering the delicate smell of monoterpenols.

SUMMARY OF THE INVENTION

Accordingly, the present invention provides a stable esterase extracted from a natural plant source.

In one embodiment of the invention, the plant tissues are selected from inflorescence of palmarosa, leaf tissues of lemongrass and some other aromatic plants.

In another embodiment of the invention, the esterase enzyme is a site specific monoterpenyl ester hydrolase capable of removing the terminal ester group of acyclic monoterpenyl esters.

In another embodiment of the invention, the esterase enzyme is stable when stored at 4° C. for one week with only 40% loss of activity.

In yet another embodiment of the invention, the esterase enzyme from palmarosa inflorescence is most active in the alkaline pH range between 8.0–9.0 and temperature range between 20–40° C.

In a further embodiment of the invention, optimum activity of the esterase enzyme is found at pH 8.5 and temperature 30° C.

In yet another embodiment of the invention, the esterase enzyme has a linear catalytic rate of up to six hours of incubation at 30° C.

The present invention also relates to a process for the extraction of a stable esterase from plant tissues from a natural source and useful for the cleaving of acyclic monoterpenyl esters into their corresponding alcohols, said process comprising: homogenizing the plant tissue in a cold extraction medium (1 g tissue/3 ml) consisting of 0.1 M NaPi buffer (pH 6.5) containing 50 mM sodium metabisulphite, 10 mM β-mercaptoethanol, 10 mM ascrobic acid, 0.25 M sucrose and 1 mM EDTA-Na$_2$, squeezing the slurry through four layers of muslin cloth, centrifuging at 15,000 × g for 60–80 minute, adding purified amberlite XAD-4 resin to the supernatant (half of the tissue weight), keeping it for 4–6 minutes at 4° C., filtering the slurry thus obtained through muslin cloth to get a clear supernatant, which is used as a esterase enzyme source.

In another embodiment of the process of the invention, the plant tissues from a natural source are selected from inflorescence of palmarosa, leaf tissues of lemongrass and some other aromatic plants.

In another embodiment of the invention, the buffer is selected from NaPi and Tris-HCl.

The invention also relates to a process for hydrolysis of the oil containing the mixture of acyclic monoterpenyl esters into their corresponding alcohols by using the novel stable esterase of the invention.

In another embodiment of the invention, the acyclic monoterpenyl esters that are hydrolysed are selected from geranyl acetate, geranyl formate and citronellyl acetate.

In a further embodiment of the invention, 75% of the geranyl acetate was hydrolyzed to its corresponding alcohol after 24 hours of incubation.

BRIEF DESCRIPTION OF THE ACCOMPANYING DRAWINGS

FIG. 1 of the accompanying drawings is a gas liquid chromatogram (GLC) depicting the activity of the an esterase of the invention obtained from palmarosa inflorescence on the cleaving of geranyl acetate to geraniol.

DETAILED DESCRIPTION OF THE INVENTION

Palmarosa (*Cymbopogon martinii*, Roxb. Wats. var. motia cv. Trishna) plants were raised from seedlings at the experimental farm of Central Institute of Medicinal and Aromatic Plants (CIMAP), Lucknow, by following standard agronomic practices. The extraction of the esterase enzyme was optimized with respect to buffer, pH, protecting and stabilizing agents to obtain maximum extractable activity. All the operations of enzyme isolation were carried out at 0–4° C. unless specified.

The extraction medium for the esterase enzyme consisted of 0.1 M NaPi buffer (pH 6.5) containing 50 mM sodium metabisulphite, 10 mM β-mercaptoethanol, 10 mM ascrobic acid, 0.25 M sucrose and 1 mM EDTA-Na$_2$. Tissue (palmarosa inflorescence) was homogenized in cold extraction medium (1 g tissue/3 ml) in the presence of 50% (w/w) insoluble PVPP (polyvinyl polypyrrolidone), which prevent enzymic browning of the homogenate. The slurry was squeezed through four layers of muslin cloth and centrifuged at 15,000×g for 60 min. Purified amberlite XAD-4 resin (50% of the tissue weight) was added to the supernatant and kept for 5 minutes at 4° C., to remove the endogenous terpenes of the tissue, which can produce a significant artefact in the determination of esterase enzyme activity. The slurry thus formed was filtered through muslin cloth and the clear supernatant obtained was used to determine the acyclic monoterpenyl esters cleaving esterase activity using geranyl acetate as a model substrate. This supernatant fraction was also used for ammonium sulphate fractionation of the esterase enzyme.

An investigation was undertaken to demonstrate the enzymic conversion of acyclic monoterpenyl esters into their corresponding monoterpenols from crude enzymic preparation of palmarosa inflorescence and the nature of the enzyme involved in the catalysis. Preliminary enzyme assays were done to optimize the assay conditions, and linearity of the reaction rate with time as well as enzyme concentration. The terpenoid substrates were solubilized by its dispersion in the solution of Tween-20 (10 μg/μmol of the substrate). A gas liquid chromatographic (GLC) procedure has been developed to detect the acyclic monoterpenyl esters cleaving esterase activity. Various kinetic properties of this esterase enzyme has been demonstrated by using geranyl acetate as substrate. Saturating levels (10 μmol) of the substrate geranyl acetate and 0.5 to 1.0 mg of the enzyme protein were used in each assay. The esterase enzyme was found to be most active in the alkaline pH range between 8.0–9.0, and showed maximal activity at pH 8.5 (0.05 M Tris-HCl) and temperature 30° C.

Figure 1A:
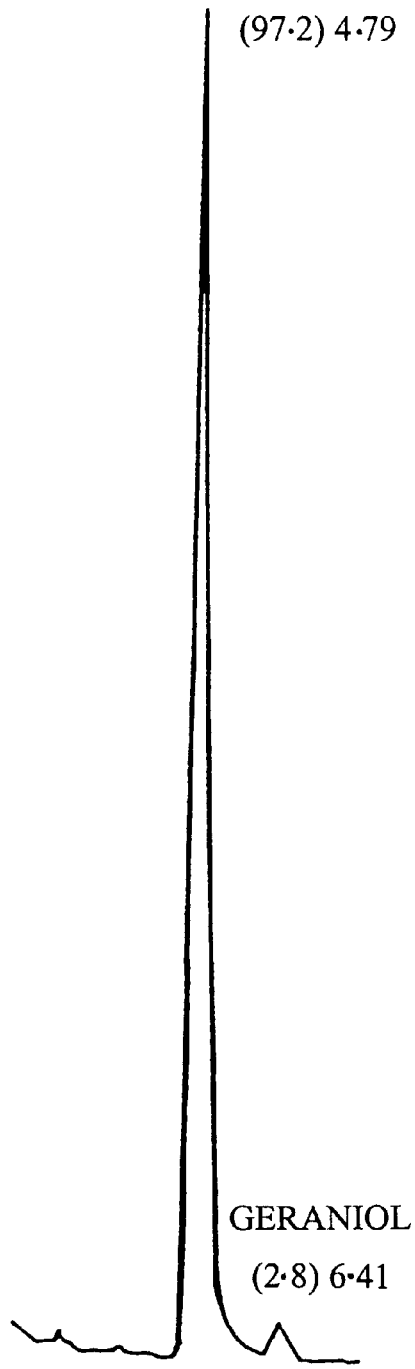
Figure 1B:
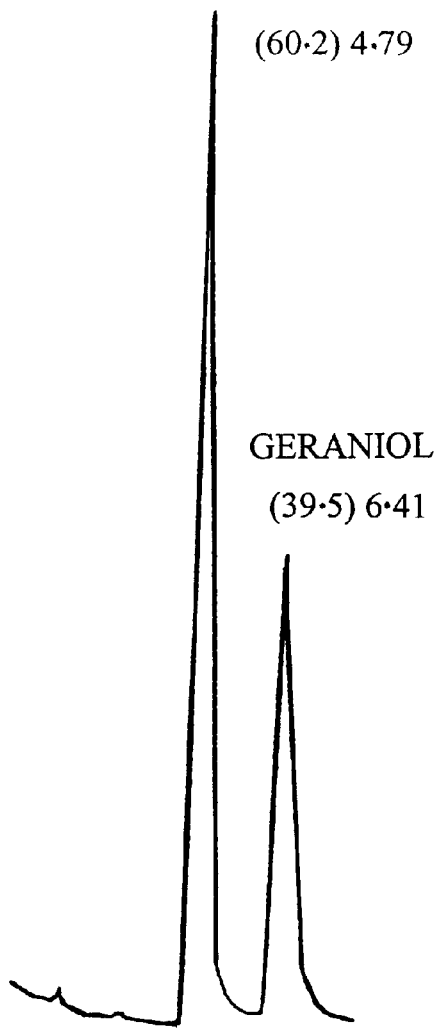

The geranyl acetate cleaving esterase activity was determined by GLC monitoring of geraniol produced by the hydrolysis of geranyl acetate. The assay system consisted of 0.05M Tris-HCl buffer (pH 8.5), 5 mM MgCl$_2$. 6H$_2$O, 1 mM DTE, 2 mM geranyl acetate and enzyme extract (approximately 1 mg protein), in a total volume of 0.5 ml. The reaction mixture was incubated at 30° C. in a sealed capped tube for 3–4 hours. The geraniol produced and leftover geranyl acetate was then extracted with ether and subjected to GLC. The appearance of geraniol peak indicated the presence of geranyl acetate cleaving esterase activity (FIG. 1). A blank with the boiled enzyme was also run simultaneously.

The gas liquid chromatographic (GLC) analysis, for the determination of geraniol produced and leftover geranyl acetate, was performed using a Perkin Elmer (model 3920 B) apparatus equipped with FID (flame ionization detector) stainless steel column (2 m×3 mm i.d.) packed with 10% FFAP (free fatty acid phase) on chromosorb WAW (80–100 mesh). The operating conditions were: Column temperature isothermal at 165° C., injector and detector temperature 200° C. and 250° C. respectively. Nitrogen and hydrogen flow rate were adjusted to 30 ml/min and 28 ml/min, respectively. The geraniol and geranyl acetate peaks were identified by coinjecting authentic standards and quantified using a Varian integrator (model 4400).

EVIDENCE FOR STABILITY OF THE ENZYME

Figure 2:
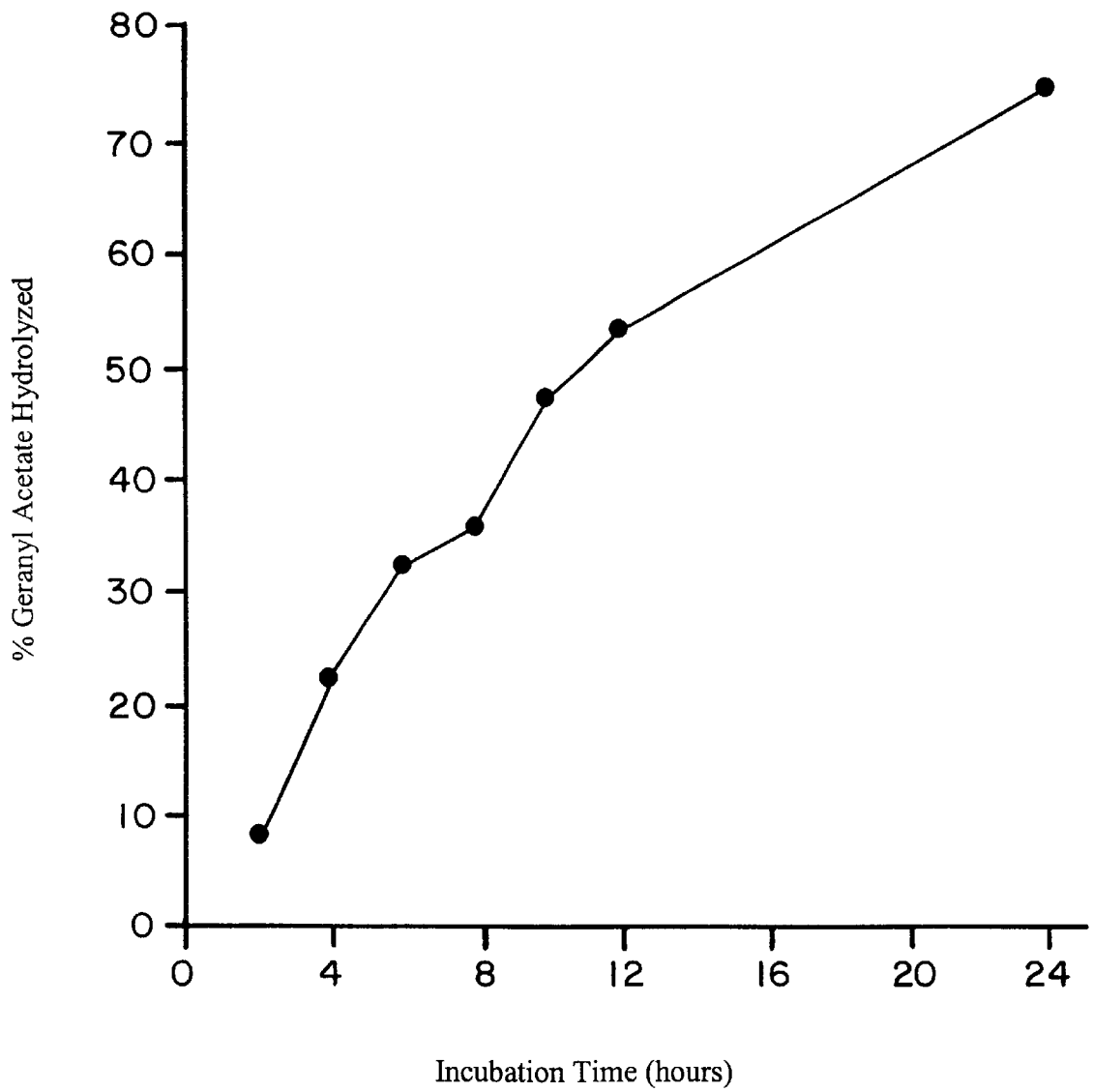
FIG. 2 is a depiction of the time course hydrolysis of geranyl acetate by an enzymatic preparation of the invention obtained from palmarosa inflorescence.

Time course experiment was performed to study the linearity of the hydrolysis of geranyl acetate during the incubation period using enzymic preparation from palmarosa inflorescence. A linear catalytic rate was found upto six hours of incubation at 30° C. Almost 75% of the geranyl acetate was hydrolyzed after 24 hours of incubation (Table 1; FIG. 2). The enzyme in the crude preparation, when stored at 4° C., was found to be quite stable for one week with 40% loss of activity.

HYDROLYSIS OF MIXTURE OF ACYCLIC MONOTERPENYL ESTERS BY THE ENZYME

Figure 3A:
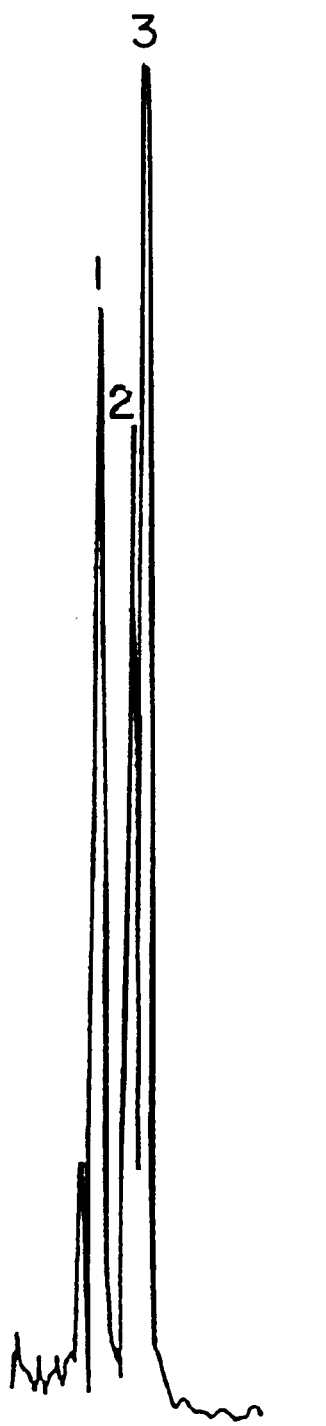
FIG. 3 is a gal liquid chromatogram (GLC) depicting the hydrolysis of a mixture of acyclic monoterpenyl estes to their corresponding alcohols.
Figure 3B:
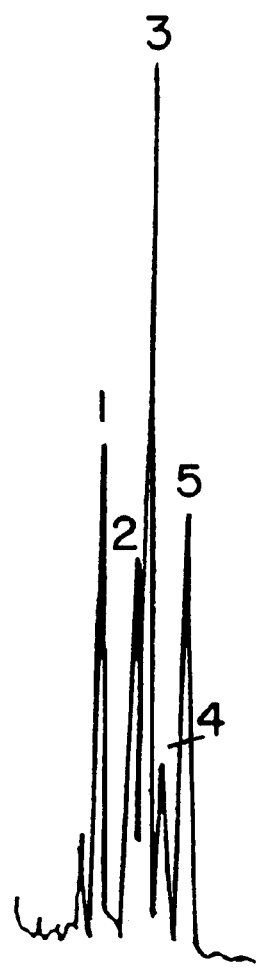

Monoterpenyl ester rich fraction from citronella java containing geranyl acetate, geranyl formate and citronellyl acetate in proportion (60:18:21) was used as substrate. The ammonium sulphate precipitated protein (60–80% fraction) was used to study the hydrolysis of these monoterpenyl esters as it was found to be rich in the monoterpenyl esters cleaving esterase activity. Apart from geranyl acetate, the enzymic preparation from palmarosa inflorescence could also hydrolyze other monoterpenyl esters such as geranyl formate and citronellyl acetate (Table 2; FIG. 3). Furthermore, crude esterase enzyme was also able to cleave these acyclic monoterpenyl esters but to a lesser extent.

SALIENT FEATURES OF THE ESTERASE ENZYME

The important properties of the esterase enzyme from palmarosa inflorescence has been summarized as follows.

The esterase enzyme from crude preparation of palmarosa inflorescence has shown the capability to cleave some acyclic monoterpenyl esters such as geranyl acetate, geranyl formate, citronellyl acetate etc., into their corresponding monoterpenyl alcohols, which are usually present as important constituents of the essential oils derived from various aromatic plant species.

The esterase enzyme showed most of the activity in the alkaline pH range and the activity is completely lost in the neutral and acidic pH range. The maximum esterase activity was found at pH 8.5 (0.05 M Tris-HCl), and temperature 30° C.

The esterase activity increased linearly with protein concentration upto 1.0 mg per assay. The crude enzymic preparation from palmarosa inflorescence, however, showed relatively less activity with NaPi buffer as compared to Tris-HCl buffer of same pH and concentrations.

Hydrolysis of geranyl acetate using enzymic preparation from palmarosa inflorescence showed linear catalytic rate upto 6 hours of incubation at 30° C. using 1 mg of crude protein. 32% of the geranyl acetate was hydrolyzed during this period, whereas, approximately 75% of geranyl acetate was hydrolyzed after 24 hours of incubation (FIG. 2). No geraniol was produced in the control using boiled enzyme.

Esterase enzyme was found to be quite stable in crude enzymic preparation from palmarosa inflorescence, when stored at 4° C. for one week, with only 40% loss of esterase activity.

Furthermore, apart from geranyl acetate, the crude enzymic preparation from palmarosa inflorescence containing esterase activity, could also hydrolyze other acyclic monoterpenyl esters such as citronellyl acetate and geranyl formate (FIG. 3), which are normally present as major constituents in essential oils from various aromatic plants.

The esterase from palmarosa inflorescence is therefore found to be not specific for monoterpenyl or ester moiety to catalyze the deesterification reaction. Thus the esterase enzyme seems to be a site-specific monoterpenyl ester hydrolase, which is capable of removing the terminal ester group of acyclic monoterpenyl esters.

TABLE 1

Time course of geranyl acetate hydrolyzed using enzymic preparation from *palmarosa inflorescence*

| S. No. | Incubation time (hour) | % Geranyl acetate hydrolyzed* |
| --- | --- | --- |
| 1. | 2 | 8.2 |
| 2. | 4 | 22.3 |
| 3. | 6 | 32.0 |
| 4. | 8 | 35.7 |
| 5. | 10 | 47.1 |
| 6. | 12 | 53.2 |
| 7. | 24 | 74.7 |

*10 μmol of geranyl acetate and 1 mg of protein were used in each assay.

TABLE 2

Hydrolysis of monoterpenyl esters by enzymic preparation (60–80% ammonium sulphate precipitated fraction) from *Palmarosa inflorescence*

| | % esters hydrolyzed* per 3 hours | | |
| --- | --- | --- | --- |
| Protein fraction | Geranyl acetate | Geranyl formate | Citronellyl acetate |
| 60–80% fraction | 19.23 | 4.86 | 6.78 |

*1 mg protein was used in the assay.

NOVELTY OF THE ENZYME

Monoterpene alcohol-monoterpenyl esters pairs occur widely in essential oils from several aromatic plant species. Monoterpenyl esters are known to mask the subtle aroma of the monoterpenols. The novelty of the esterase enzyme from palmarosa inflorescence lies in its non-specificity towards acyclic monoterpenyl esters. A variety of acyclic monoterpenyl esters can be hydrolyzed using this enzyme to produce monoterpenols, and thereby recovering the subtle aroma of the monoterpenols. Thus, the non-specific nature of the esterase enzyme from palmarosa inflorescence can be exploited in perfumary and cosmetic industry to recover the delicate smell of the monoterpenols. Furthermore, the monoterpenols produced by biotechnological approaches is preferred as compared to those produced by chemical hydrolysis.

ADVANTAGES

1. The novel esterase enzyme from crude preparation of palmarosa inflorescence has shown the capability to cleave some acyclic monoterpenyl esters into their corresponding monoterpenyl alcohols.
2. The esterase enzyme from palmarosa inflorescence showed most of the activity in the alkaline pH range and the activity is completely lost in the neutral and acidic pH range, with optimum activity at pH 8.5 (0.05 M Tris-HCl buffer) and temperature 30° C.
3. The esterase enzyme activity increased linearly with protein concentration upto 1.0 mg per assay.
4. Esterase enzyme was found to be quite stable in crude enzymic preparation from palmarosa inflorescence, when stored at 4° C. for one week, with only 40% loss of esterase activity.
5. The esterase enzyme from palmarosa inflorescence is found to be a site-specific monoterpenyl ester hydrolase, which is capable of removing the terminal ester group of acyclic monoterpenyl esters, and thereby producing monoterpenyl alcohols.

We claim:

1. A stable esterase obtained from plant tissues of palmarosa, wherein said esterase is a monoterpenyl ester hydrolase.

2. A stable esterase as claimed in claim 1 wherein the plant tissues are inflorescence of palmarosa.

3. A stable esterase of claim 1 wherein the esterase is stable when stored at 4° C. for one week.

4. A stable esterase as claimed in claim 2 wherein the esterase is active in the alkaline pH range between 8.0–9.0 and temperature range between 20–40° C.

5. A stable esterase as claimed in claim 4 wherein optimum activity is found at pH 8.5 and temperature 30° C.

6. A stable esterase as claimed in claim 1 having a linear catalytic rate of up to six hours of incubation at 30° C.

7. A stable esterase as claimed in claim 1 being a site specific monoterpenyl ester hydrolase capable of removing the terminal ester group of acyclic monoterpenyl esters, thereby producing monoterpenyl alcohols.

* * * * *